United States Patent [19]

White

[11] E Patent Number: Re. 32,598

[45] Reissued Date of Patent: Feb. 9, 1988

[54] FEATURE EXTRACTION SYSTEM FOR EXTRACTING A PREDETERMINED FEATURE FROM A SIGNAL

[76] Inventor: John U. White, Contentment Island Rd., Darien, Conn. 06820

[21] Appl. No.: 524,696

[22] Filed: Aug. 19, 1983

Related U.S. Patent Documents

Reissue of:

[64] Patent No.: 4,022,529
Issued: May 10, 1977
Appl. No.: 639,804
Filed: Dec. 11, 1975

U.S. Applications:

[63] Continuation of Ser. No. 036,994, May 8, 1979, abandoned.

[51] Int. Cl.[4] ..... G01N 21/64; G01N 21/65

[52] U.S. Cl. ..... 356/318; 250/458.1; 356/301; 356/324

[58] Field of Search ..... 356/301, 317, 318; 250/458.1, 459.1, 461.1; 350/420, 421

[56] References Cited

U.S. PATENT DOCUMENTS

| | | | |
|---|---|---|---|
| 2,940,355 | 6/1960 | Cary | 356/301 |
| 3,191,488 | 6/1965 | Eisner . | |
| 3,204,105 | 8/1965 | Robinson . | |
| 3,359,056 | 12/1967 | Offner . | |
| 3,414,354 | 12/1968 | Siegler, Jr. | 356/301 |
| 3,516,744 | 6/1970 | Hinman et al. | 356/301 |
| 3,520,614 | 7/1970 | Goldstein | 356/325 |
| 3,542,481 | 11/1970 | Slomba | 356/244 |
| 3,545,869 | 12/1970 | Auphan . | |
| 3,556,659 | 1/1971 | Hawes | 356/301 |
| 3,606,547 | 9/1971 | Iwahashi | 356/325 |
| 3,678,272 | 7/1972 | Jasny . | |
| 3,748,040 | 7/1973 | Hawes . | |
| 3,825,555 | 8/1974 | Ohnishi | 356/317 |
| 3,825,762 | 7/1974 | White | 356/324 |
| 3,975,098 | 8/1976 | West | 356/323 |
| 4,076,420 | 2/1978 | De Maeyer et al. | 356/317 |

OTHER PUBLICATIONS

Oldenberg; "On the Intensity of Illumination in Spectrographs" JOSA, vol. 22 #8, Aug. 1932, pp. 441–455.
Richardson; "An Image Slicer for Spectrographs" Publications of The Astronomical Society of the Pacific (PASP) vol. 78 #pp. 436 & 437.
"The SPF-1000", Bulletin 2423-1, American Instrument Co., Inc., Silver Springs, Maryland 20910, printed in U.S.A. Feb. 1968.
Brochure by Farrand Optical Co. 1974.
"Analytical Biochemistry" vol. 16, pp. 438–449, 1966.
Cary Instruments brochure 1968.
"Spectroscopy" pp. 290–293, Oct. 10, 1974.
"JASCO-Report" vol. 11, No. 10, Oct. 25, 1974.
Diagram entitled "FP-4 Fluoresence Spectrophotometer" (undated).
"Model FP-4 Fluorescence Spectrophotometer," Japan Spectroscopic Co. Ltd. Feb. 1974.
Sheet entitled "JASCO MPF-4 Optional Accessories" (undated).
Brochure entitled "Model FP-3 Hitachi Fluorescence Spectrophotometer" (undated).
"Fluorescence Lifetimes: Theory, Instrumentation, and Application of Nanosecond Fluorometry"; Spencer pp. 104–122; 1970.

*Primary Examiner*—Vincent P. McGraw
*Attorney, Agent, or Firm*—Lee C. Robinson, Jr.

[57] ABSTRACT

A fluorescence spectrophotometer in which the optical system for the excitation monochromator includes an arrangement for forming an image of the exit slit of the monochromator adjacent a first surface of the sample being evaluated and for forming an aperture image adjacent a second surface of the sample. Fluorescence from the sample is directed to an emission monochromator which likewise has an arrangement for forming an image of the emission monochromator's entrance slit adjacent a third surface of the sample and for forming an aperture image adjacent a fourth surface. The optical components are arranged such that the images of the slits lie in a single plane defined by the axial rays of the excitation and fluorescence beams, and in several advantageous arrangements the slit images are oriented at 90° from the slits themselves. The intensity of the output signal may be further increased by locating mirrors behind the sample holder to direct the light back through the sample for a second pass.

This is a Reissue of a Patent which was the subject of a Reexamination Certificate No. B1 4,022,529, dated May 10, 1977, Request No. 90/000,155.

7 Claims, 7 Drawing Figures

FEATURE EXTRACTION SYSTEM FOR EXTRACTING A PREDETERMINED FEATURE FROM A SIGNAL

Matter enclosed in heavy brackets [ ] appears in the original patent but forms no part of this reissue specification; matter printed in italics indicates the additions made by reissue.

*This application is a continuation of Ser. No. 36,994, filed May 8, 1979 and now abandoned.*

BACKGROUND OF THE INVENTION

This invention relates to radiation measuring apparatus and more particularly to fluorescence spectrophotometers of the type in which a sample is irradiated with light of one wavelength and its emission spectrum is observed through the use of a monochromator and a detection system. As used herein and in the appended claims, the term "light" includes not only visible light but also radiation having wavelengths longer and shorter than the visible spectrum.

In the measurement of fluorescence and exitation spectra it is customary to illuminate a sample with monochromatic light from an intense source and to observe the light emitted by the sample with a monochromator and a photoelectric detection system. Either the excitation or the emission wavelength may be scanned to record the intensity of the spectrum as a function of excitation or emission wavelength.

Heretofore, radiation measuring apparatus of the foregoing type exhibited certain disadvantages. One of the more significant problems was the comparatively low intensity of the output signal particularly in measuring the spectra of dilute materials. In the usual form of apparatus a magnified image of the light source was focused on the entrance slit of the excitation monochromator, and a reduced image of the exit slit was focused on the sample by means of a first optical system. Fluorescence from the sample was collected by a second optical system and was focused on the entrance slit of an emission monochromator such that the signal at the exit slit of this latter monochromator was proportional to the intensity of the light at the selected wavelength. Attempts to increase the intensity of the signal commonly included a reduction in height of the image of the excitation monochromator's exit slit. These attempts were only partialy successful, however, and the measured intensity continued to be insufficient to obtain readings of the desired accuracy for low intensity samples.

SUMMARY

One general object of this invention, therefore, is to provide new and improved apparatus for measuring the intensity of light emitted by a sample with respect to the intensity of the light exciting the sample.

More specifically, it is an object of this invention to provide radiation measuring apparatus which is effective to produce a high intensity fluorescence signal.

Another object of the invention is to provide a fluorescence spectrophotometer utilizing comparatively simple optical components which is economical to manufacture and reliable in operation.

In a preferred embodiment of the invention, the apparatus comprises a radiation source and an excitation monochromator for isolating an excitation beam of monochromatic radiation from the source. The excitation monochromator includes first and second limiting apertures for the monochromatic radiation which are respectively formed by the excitation exit slit and the monochromator's dispersing means. The radiation is received by a first optical system, and is directed toward the sample being evaluated to cause the sample to emit fluorescence. A second optical system collects fluorescence from the sample and focuses a beam of the collected radiation on the entrance slit of an emission monochromator to produce a monochromatic emission beam at the monochromator's exit slit. In a manner similar to that of the excitation monochromator, the emission monochromator includes third and fourth limiting apertures which are formed by the emission entrance slit and the dispersing means and are imaged adjacent the sample. The emission beam from the exit slit is received by a photoelectric detector to provide a signal proportional to the intensity of the fluorescent light emitted by the sample at the selected wavelength.

In accordance with one feature of the invention, the longitudinal axes of the slit images adjacent the sample lie in a single plane defined by the axial rays of the excitation and fluorescence beams. In some cases this is accomplished by an anamorphic mirror and lens arrangement in each of the optical systems which orients the images at ninety degree angles with respect to the exit and entrance slits of the respective excitation and emission monochromators, while in other embodiments the slits themselves are oriented parallel to the plane. The arrangement is such that each point along the entrance slit of the emission monochromator is filled with light of an intensity corresponding to illumination of the sample with light from all points along the length of the excitation monochromator's exit slit, with the result that a very substantial increase in the intensity of the output signal is achieved.

In accordance with another feature of several particularly advantageous embodiments of the invention, an image of the first limiting aperture is formed adjacent a first surface of the sample, and an image of the second limiting aperture is formed adjacent a second surface of the sample. Similarly, an image of the third limiting aperture is formed adjacent a third surface of the sample, and an image of the fourth limiting aperture is formed adjacent a fourth surface of the sample. *For a particular instrument employing simple lenses the positions of the various images relative to the sample will of course change during variations in wavelength, but in these embodiments it is important that a given image be located adjacent the specified sample surface over at least a substantial portion of the wavelength range for which the instrument is designed.* The widths of the slits advantageously are of the same order of magnitude, and the magnification is chosen to make the height of each radiation beam passing through the sample about the same at each of the sample surfaces, to provide an additional improvement in the output intensity.

In accordance with a further feature of certain embodiments of the invention, the extreme rays between the images of the two apertures in the excitation monochromator illuminate a sample volume in the approximate shape of a right rectangular prism, and the extreme rays between the two images of the apertures in the emission monochromator are illuminated from a sample volume which similarly is in the shape of a right rectangular prism. The width of the beam passing through the sample is comparatively uniform and is maintained as small as practical, with the result that the intensity of the output signal is further increased.

The present invention, as well as further objects and advantages thereof, will be understood more clearly and fully from the following description of certain preferred embodiments, when read with reference to the accompanying drawings.

DESCRIPTION OF CERTAIN PREFERRED EMBODIMENTS

Figure 1:
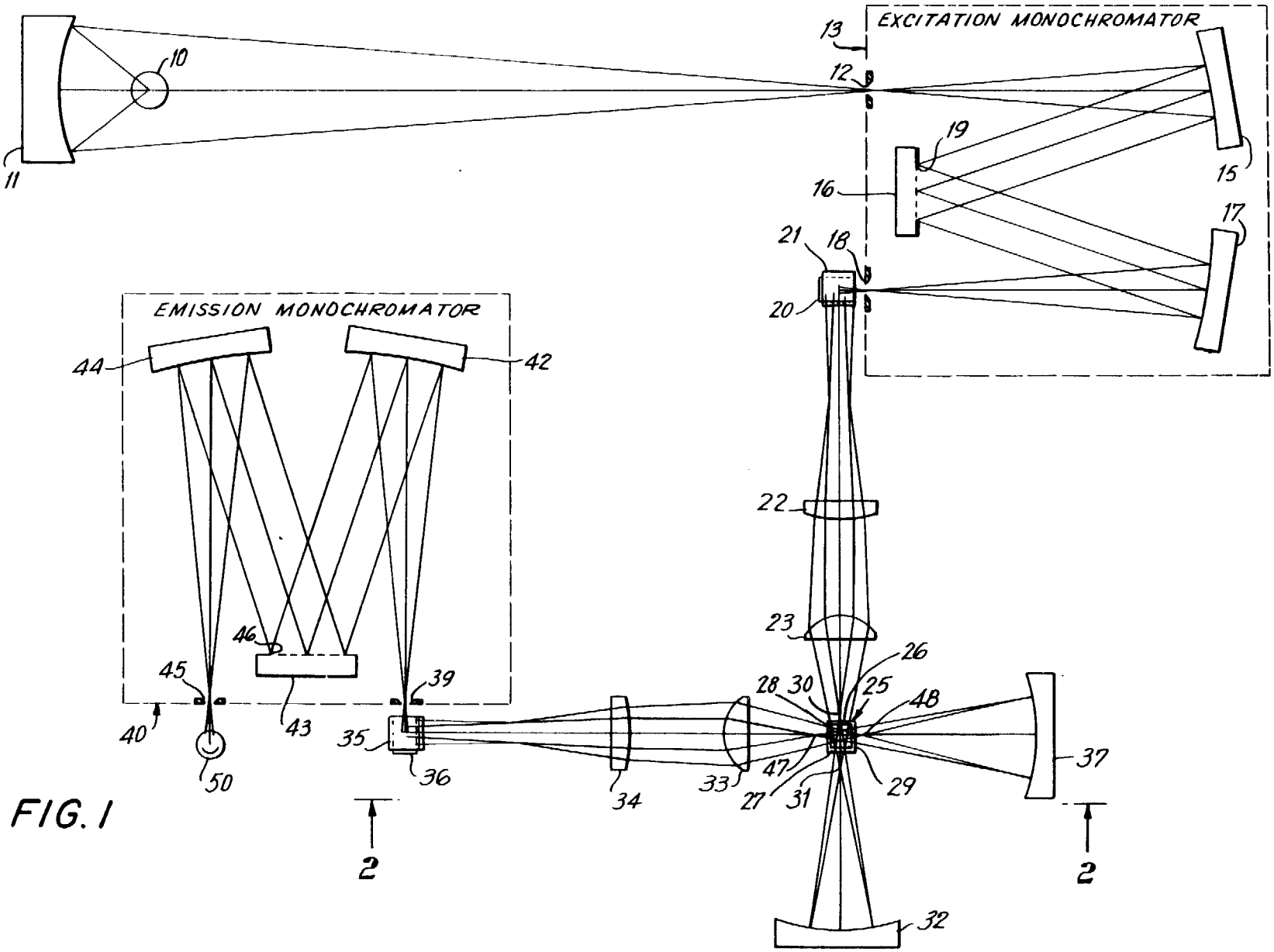
FIG. 1 is a simplified schematic plan view of a fluorescence spectrophotometer in accordance with one illustrative embodiment of the invention.

Referring to FIG. 1 of the drawings, there is shown a schematic representation of a fluorescence spectrophotometer having a xenon arc or other suitable source 10 of visible or invisible light. Light from the source 10 is collected by an ellipsoidal mirror 11 and is focused onto the entrance slit 12 of an excitation monochromator 13. The entrance slit 12 is of rectangular configuration with its longitudinal axis extending in a direction perpendicular to the plane of the drawing. The monochromator 13 is of the [Ebert] *Czerney-Turner* type and includes, in addition to the entrance slit 12, a collimating mirror 15, a diffraction grating 16, a telescope mirror 17 and an exit slit 18 which likewise has its longitudinal axis extending perpendicular to the plane of the drawing. The light entering the entrance slit 12 is reflected by the mirror 15 to the grating 16 and then from the mirror 17 to the exit slit 18. The periphery of the grating 16 forms a limiting aperture 19, for purposes that will become more fully apparent hereinafter.

The light emerging from the excitation slit 18 is in the form of a monochromatic excitation beam. The monochromatic beam is received by a first optical system which comprises superimposed flat and spherical mirrors 20 and 21, a cylindrical lens 22 and a spherical lens 23. The mirrors 20 and 21 are oriented at 45° angles with respect to the principal ray of the incident beam to direct the light upwardly and then horizontally toward the lenses 22 and 23. The mirrors 20 and 21 reflect the excitation beam at right angles to its original direction.

Figure 1A:
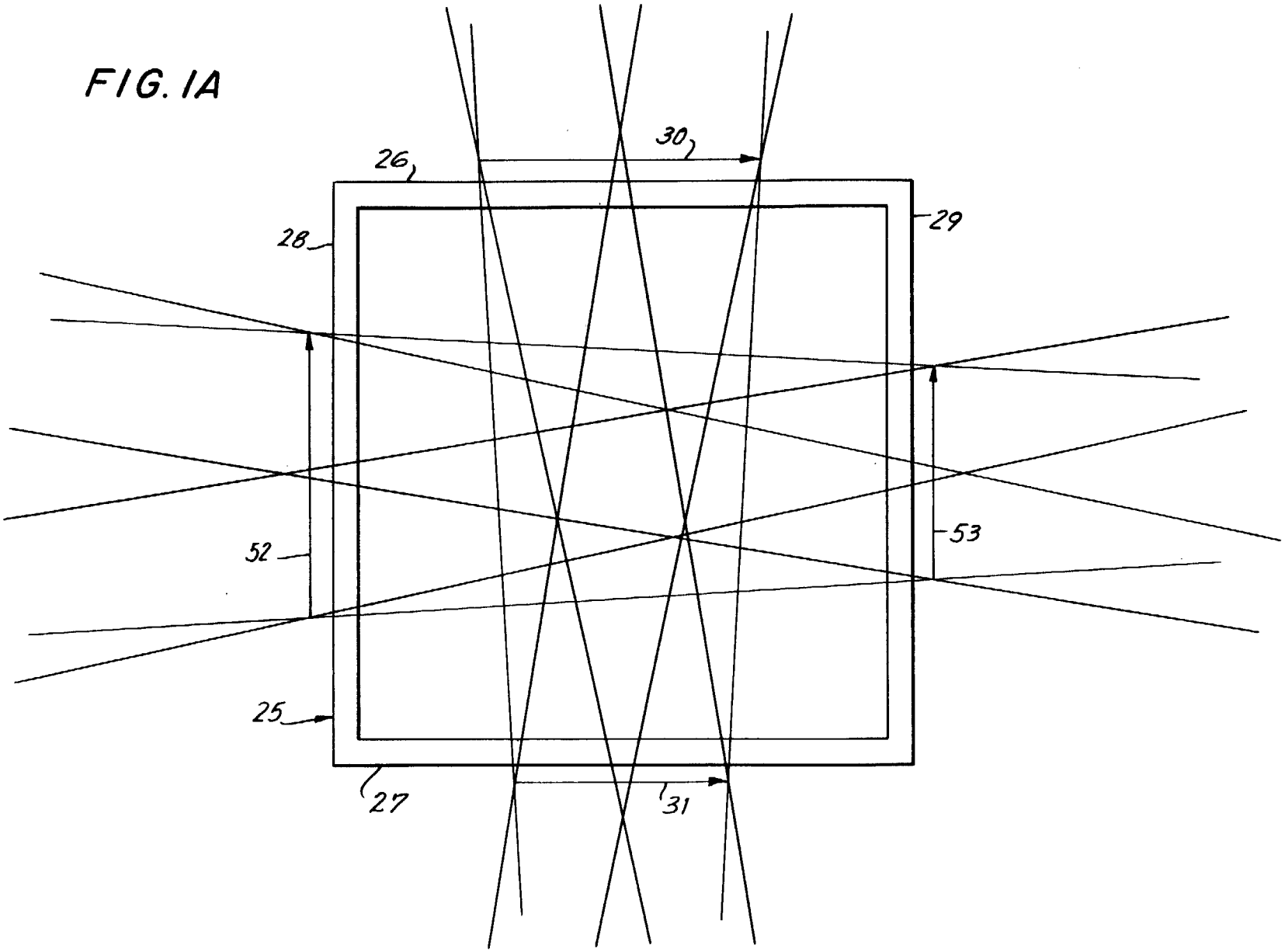
FIG. 1A is an enlarged schematic plan view of the light paths adjacent the sample holder of the spectrophotometer shown in FIG. 1.
Figure 1B:
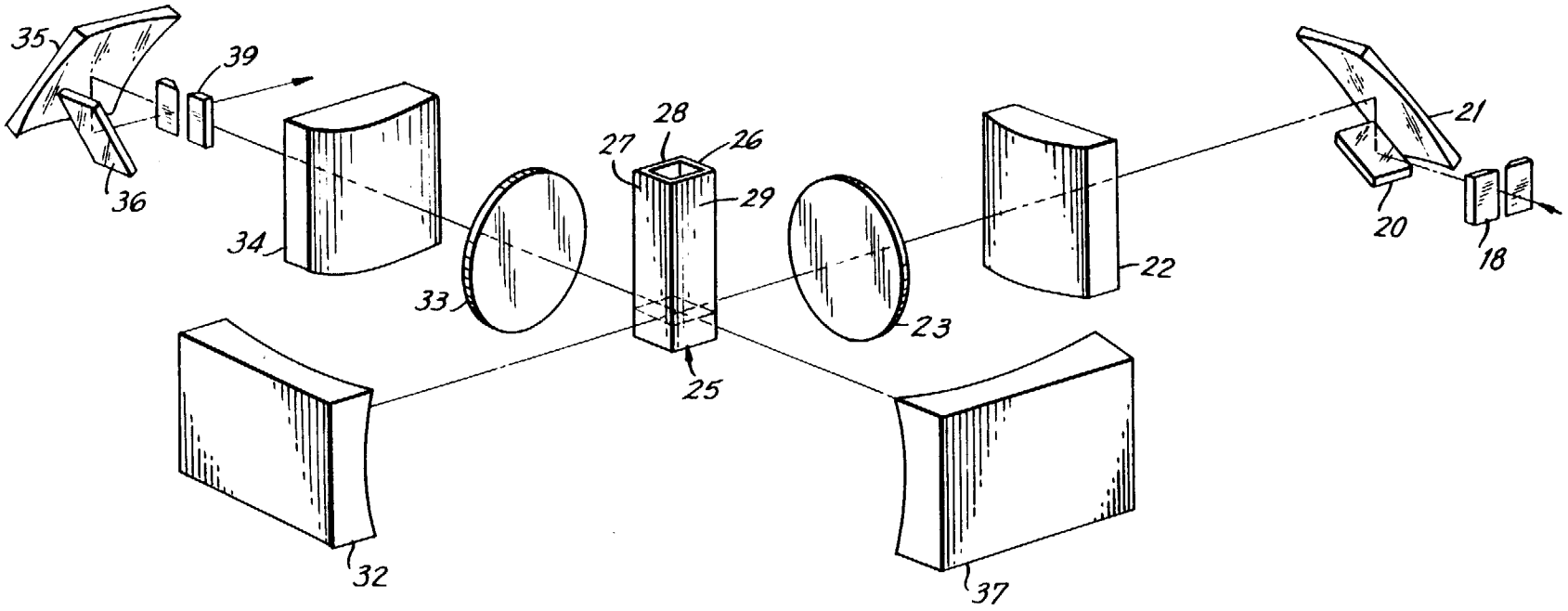
FIG. 1B is an enlarged fragmentary isometric view of the sample holder and optical systems for the spectrophotometer of FIG. 1.

The convex spherical lens 23 focuses the excitation beam on a sample holder or cell indicated generally at 25. The sample cell 25 is of square configuration and includes opposed pairs of flat surfaces 26 and 27, and 28 and 29. As best shown in FIG. 1A, the lens 23 forms a real horizontal image 30 of the aperture defined by the excitation exit slit 18. The image 30 is located closely adjacent the surface 26 of the sample cell 25.

In addition to the excitation exit slit image 30, the first optical system is effective to form an image 31 of the grating aperture 19. The image 31 is located in close proximity with the surface 27 of the sample cell 25, that is, the surface opposite that adjacent the image 30. The longitudinal axis of each of the images 30 and 31 lies in a single plane parallel to the plane of the drawing.

It will be noted that the flat angular mirror 20 and the spherical angular mirror 21 serve to orient the images 30 and 31 at right angles to the direction of the exit slit 18. Thus, the mirrors 20 and 21 rotate the images through a 90° angle such that their longitudinal dimensions are parallel to the plane of the drawing. The mirrors 20 and 21, together with the lenses 22 and 23, form the excitation optical system for the instrument and direct the excitation beam from the exit slit 18 to the sample 25. The optical system is anamorphic, and its magnification is such that the length and width of the exit slit image 30 are approximately equal to the length and width of the aperture image 31, respectively. With this arrangement, the extreme rays between the images 30 and 31 illuminate a sample volume in the approximate shape of a right rectangular prism. The width of the beam passing through the sample is comparatively uniform and is maintained as small as practical, with the result that the intensity of the beam is substantially increased.

To provide a further increase in the intensity of the light beam passing through the sample 25, a spherical mirror 32 is located a short distance behind the sample adjacent the sample surface 27 opposite that facing the excitation monochromator 13. The mirror 32 directs the excitation beam back through the sample for a second pass.

The excitation beam passing through the sample 25 excites the sample and causes it to emit fluorescence of a wavelength different from that of the exciting light. This fluorescence is emitted in all directions. A portion of the emitted fluorescence is collected by a spherical lens 33 and is directed thereby through a cylindrical lens 34 to a spherical off-axis mirror 35 and a flat off-axis mirror 36. The lenses 33 and 34 and the mirrors 35 and 36 form an anamorphic emission optical system which is identical with the excitation optical system comprising the mirrors 20 and 21 and the lenses 22 and 23. In a manner similar to that of the mirrors 20 and 21, the mirrors 35 and 36 are oriented at 45° angles with respect to the principal rays of the emission beam collected from the sample 25. To further increase the intensity of the emission beam, a spherical mirror 37 is positioned a short distance behind the sample 25 in facing relationship with the sample surface 29. The mirror 37 collects additional fluorescence from the sample and directs it through the emission optical system.

The fluorescent emission beam from the emission optical system is directed by the spherical mirror 36 to the entrance slit 39 of an emission monochromator 40. This entrance slit is of rectangular configuration and has its longitudinal axis extending in a direction perpendicular to the plane of the drawing. The monochromator 40 is similar to the excitation monochromator 13 and, in addition to the entrance slit 39, includes a collimating mirror 42, a diffraction grating 43, a telescope mirror 44 and an exit slit 45 parallel to the entrance slit. The fluorescence enters the entrance slit 39, is reflected by the collimator 42 to the grating 43 and is then focused by the telescope 44 on the exit slit 45. The periphery of the grating 43 defines a limiting aperture 46.

The light emerging from the exit slit 45 comprises a selected, highly monochromatic portion of the luminescent emission from the sample 25. The emerging light is received by a photoelectric detector 50 which is of conventional construction and preferably is of a type which exhibits high sensitivity at the particular wavelengths of interest. The detector 50 produces an output signal proportional to the intensity of the light from the exit slit 45.

The spherical lens 33 in the optical system for the emission monochromator 40 forms an optical image 52 of the aperture defined by the emission entrance slit 39. This image is located in close juxtaposition with the surface 28 of the sample cell 25. Similarly, an optical image 53 of the grating aperture 46 is formed adjacent the opposite surface 29 of the sample cell. By reason of the off-axis angular orientation of the mirrors 35 and 36, the longitudinal axes of the images 52 and 53 lie in a single plane parallel to the plane of the drawing and at right angles to the longitudinal axis of the entrance slit 39. The extreme rays between the images 52 and 53 outline a sample volume in the approximate shape of a right rectangular prism, and the width of the beam passing through the sample is comparatively uniform and is as small as practical.

The principal rays of the beam from the excitation monochromator 13 and the beam approaching the emission monochromator 40 intersect at the sample cell 25. The longitudinal axis of each of the anamorphic aperture images 30, 31, 52 and 53 lies in a plane defined by these principal rays. The exit slit 18 for the excitation monochromator 13 and the entrance slit 39 for the emission monochromator 40, on the other hand, extend in directions perpendicular to the plane defined by the principal rays. The image 30 of the exit slit 18 is parallel to the path of the emission beam, and the image 52 of the entrance slit 39 is parallel to the path of the excitation beam. The arrangement is such that each point along the entrance slit 39 is filled with light of an intensity corresponding to the irradiation of the sample with light from the entire length of the exit slit 18.

The resulting increase in the amount of fluorescent light collected by the entrance slit 39 in theory may be as large as the length to width ratio of the image 30 of the exit slit 18. In terms of the properties of the monochromators, and with slit and grating images of equal length and equal width, the ratio is equivalent to the square root of the ratio of the length of the exit slit multiplied by the angular slit aperture in a plane including the longitudinal axis of the slit divided by the width of the slit multiplied by the angular aperture at the slit in the transverse plane. Because of varying slit widths and aberrations the predicted increase, while still substantial, may not be realized particularly for comparatively large length to width ratios. In cases in which the actual height of the beam is approximately the same adjacent the opposite surfaces of the sample, however, the actual increase closely approaches the theoretical value, and signal increases may be achieved which are approximately 5 to 10 times that realized by conventional fluorescence instrumentation.

In the excitation and emission optical systems the spherical [lenses] *mirrors* introduce a degree of astigmatism in the slit and grating images. This astigmatism is corrected by the cylindrical lenses in the systems. The systems have anamorphic properties that distort the slit and grating images in such a way that they both have the same length to width ratio.

The mirrors 32 and 37 serve to direct the respective excitation and emission beams back through the sample 25 for a second pass. The mirrors 32 and 37 are spherically concave with centers of curvatures at the center of the sample. With this arrangement each of the mirrors forms an image of the facing surface of the sample adjacent the opposite surface and also forms an image of the opposite surface adjacent the facing surface. The increase in intensity as a result of these mirrors is almost four times the intensity of instruments in which the mirrors are omitted.

Figure 2:
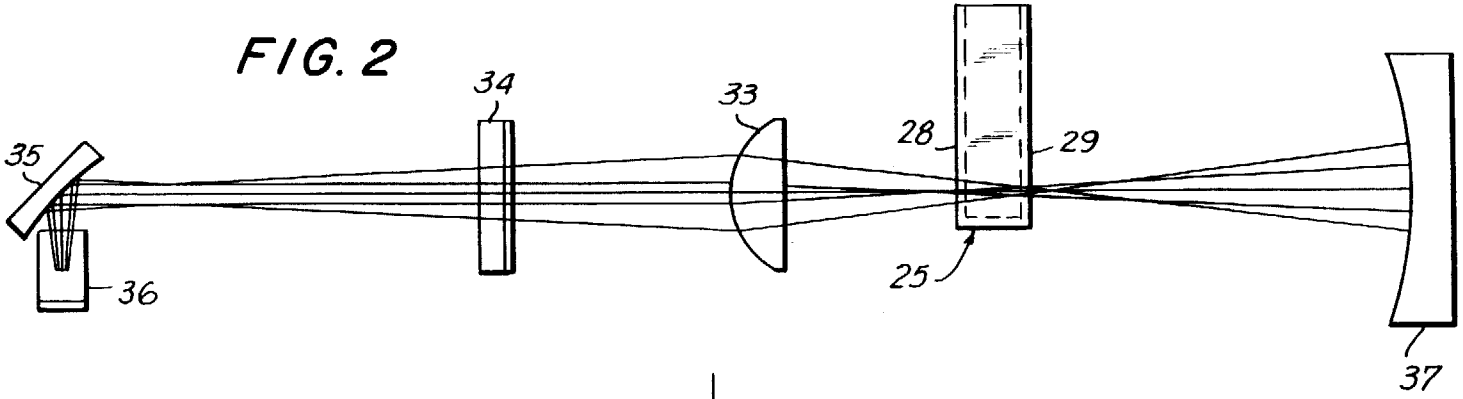
FIG. 2 is a simplified schematic elevational view of a portion of the spectrophotometer shown in FIG. 1, as seen from the line 2—2 in FIG. 1.

The embodiment illustrated in FIGS. 1 and 2 employs the respective pairs of angular mirrors 20 and 21 and 35 and 36 to orient each of the slit images 30 and 52 in a direction parallel to the direction of travel of the light of the other beam. This same result may be achieved through the use of various other optical systems which eliminate the need for angularly disposed mirrors. In the embodiment shown in FIGS. 3 and 4, for example, the slits themselves are located such that they extend in directions parallel to the direction of the opposite beam. The instrument of these latter figures includes a xenon arc light source 60 and an ellipsoidal mirror 61 which focuses the light onto the entrance slit 62 of an excitation monochromator 63. Contrary to the embodiment illustrated in FIGS. 1 and 2, the entrance slit 62 has a longitudinal axis which lies in the plane of the drawing. A selected, monochromatic portion of the light from the entrance slit 62 is reflected by a concave diffraction grating 65 onto an exit slit 70 which likewise has a longitudinal axis lying in the plane of the drawing. As in the case of the previously described embodiment, the periphery of the grating 65 forms a limiting aperture 71 for the monochromatic light.

The monochromatic excitation beam emerging from the exit slit 70 is received by a first optical system which includes a torroidal lens 72 and a beam splitter 74. The beam splitter 74 illustratively is in the form of a flat quartz plate. A known fraction of this light passes through the splitter 34 and is directed by a concave spherical mirror 75 to a convex spherical lens 76.

The lens 76 focuses the excitation beam from the mirror 75 on a sample cell 78. The configuration of the cell 78 is similar to that of the cell 25 (Fig. 1) described heretofore and includes pairs of opposed surfaces 80 and 81 and 82 and 83. The lens is effective to form a real horizontal image of the aperture defined by the excitation exit slit 18, and this image is located between the lens and the sample surface 80. Similarly, a real horizontal image of the grating aperture 71 is formed adjacent the opposite sample surface 81.

Figure 5:
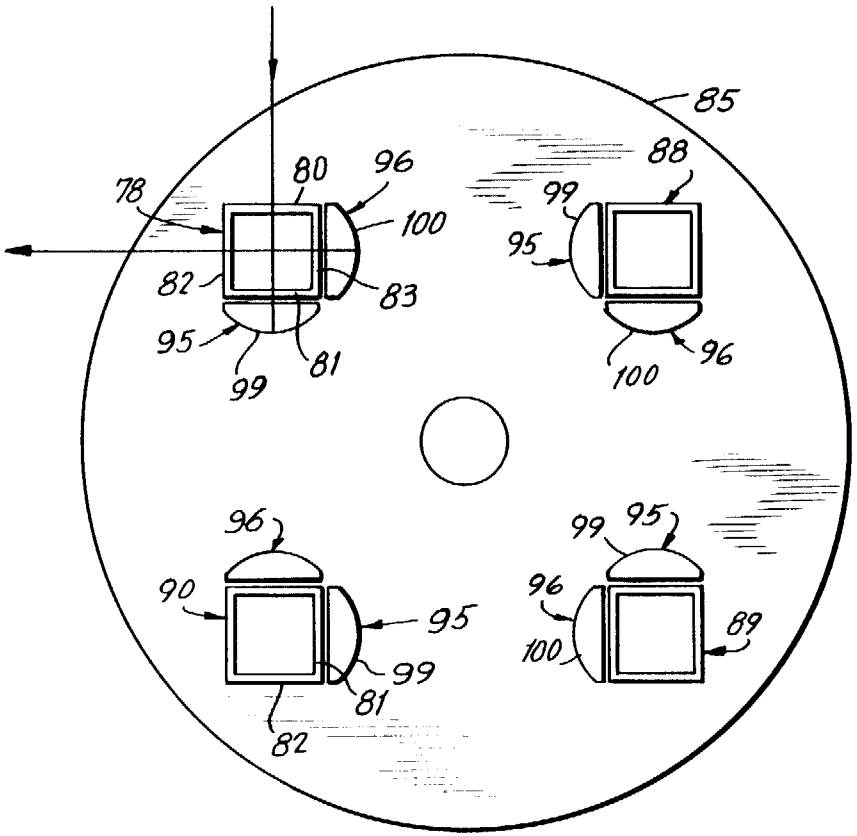
FIG. 5 is an enlarged plan view of the sample holder employed in the spectrophotometer of FIGS. 3 and 4.

As best shown in FIG. 5, the sample cell 78 is supported adjacent the periphery of a rotatable table 85. The table 85 is of circular configuration and includes three additional sample cells 88, 89 and 90 which may contain different fluorescent materials and likewise are provided with the opposed pairs of surfaces 80 and 81 and 82 and 83. The various sample cells are spaced at 90° intervals on the table 85 such that the sample being evaluated may be readily changed merely by pivoting the table through a corresponding angle.

A pair of mirrors 95 and 96 is located adjacent each of the sample cells 78,88,89 and 90 in spaced juxtaposition with the surfaces 81 and 83, respectively. The mirrors 95 and 96 are optically transparent except for spherically concave reflective surfaces 99 and 100 on their rear faces. Contrary to the sample mirrors in the embodiment of FIGS. 1 and 2, these surfaces are positioned at the approximate locations of the corresponding grating images with their centers of curvatures at the approximate locations of the associated slit images. The slit images are reimaged back on themselves to further increase the intensity of the output signal.

Fluorescence from the sample 78 is collected by a convex spherical lens 105 (FIG. 3) in the emission optical system for the instrument. The fluorescent emission beam then passes through a lens 107 and is focused by a lens 108 on the entrance slit 109 of an emission monochromator 110. The longitudinal axis of the entrance slit 109 lies in the plane of the drawing and is in coplanar relationship with that of the excitation exit slit 70.

The emission beam entering the exit slit 109 is received by a concave diffraction grating 112 having a grating aperture 113 and is directed to an exit slit 114. The longitudinal axis of this latter slit is coplanar with that of the remaining slits. The fluorescence emerging from the exit slit 114 is received by a reflecting prism 115 and is directed thereby to a photoelectric detector 116 to provide an output signal proportional to the intensity of the light from the exit slit.

The emission optical system between the sample 78 and the entrance slit 109 is optically the same as the excitation optical system between the exit slit 70 and the sample except for the use of the cylindrical lens 107 in place of the spherical mirror 75. The emission optical system forms images of the exit slit 109 and the grating aperture 113 in respective juxtaposition with the surfaces 82 and 83 of the sample.

The longitudinal axes of the excitation exit slit 70 and the emission entrance slit 109 lie in a single plane defined by the principal rays of the beam from the excitation monochromator 63 and the beam approaching the emission monochromator 110. The images of the slits 70 and 109, together with the images of the grating apertures 71 and 113, similarly have longitudinal axes which lie in this plane. As in the previously described embodiment, each point on the emission entrance slit 109 is filled with light of an intensity corresponding to the irradiation of the sample with light from the entire length of the excitation exit slit 70. The resulting increase in intensity is further enhanced through the use of the mirrors 95 and 96 adjacent the sample cell in the manner described heretofore.

As has been explained, the beam splitter 74 serves to pass a known fraction of the light from the excitation monochromator 63 to the mirror 75, the lens 76 and the sample 78. The remaining fraction is reflected by the splitter 75 through successive lenses 122 and 123 to the reflection prism 115 and then to the photoelectric cell 116. The remaining fraction is used as a reference beam and is periodically interrupted by a continuously rotating chopper 120 between the lens 123 and the photocell 116. The chopper 120 is oriented between the lenses 107 and 108 in position to also periodically interrupt the fluorescent emission beam. As will be understood, the chopper is provided with suitable cutouts (not visible in the drawings) to simultaneously admit fluorescence to the photocell and block the reference beam and to thereafter block the fluorescent beam and pass the reference beam to the photocell.

The photoelectric cell 116 is thus alternately illuminated by light from the luminescent sample 78 and by reference light from the excitation monochromator 63. The light detected by the photocell is alternately representative of the unknown luminescent intensity from the sample and the intensity of the reference beam.

Through the use of conventional electrical circuitry, the output signals from the photocell may be translated into a net output signal corresponding to the ratio of the net sample signal to the net reference signal.

Figure 3:
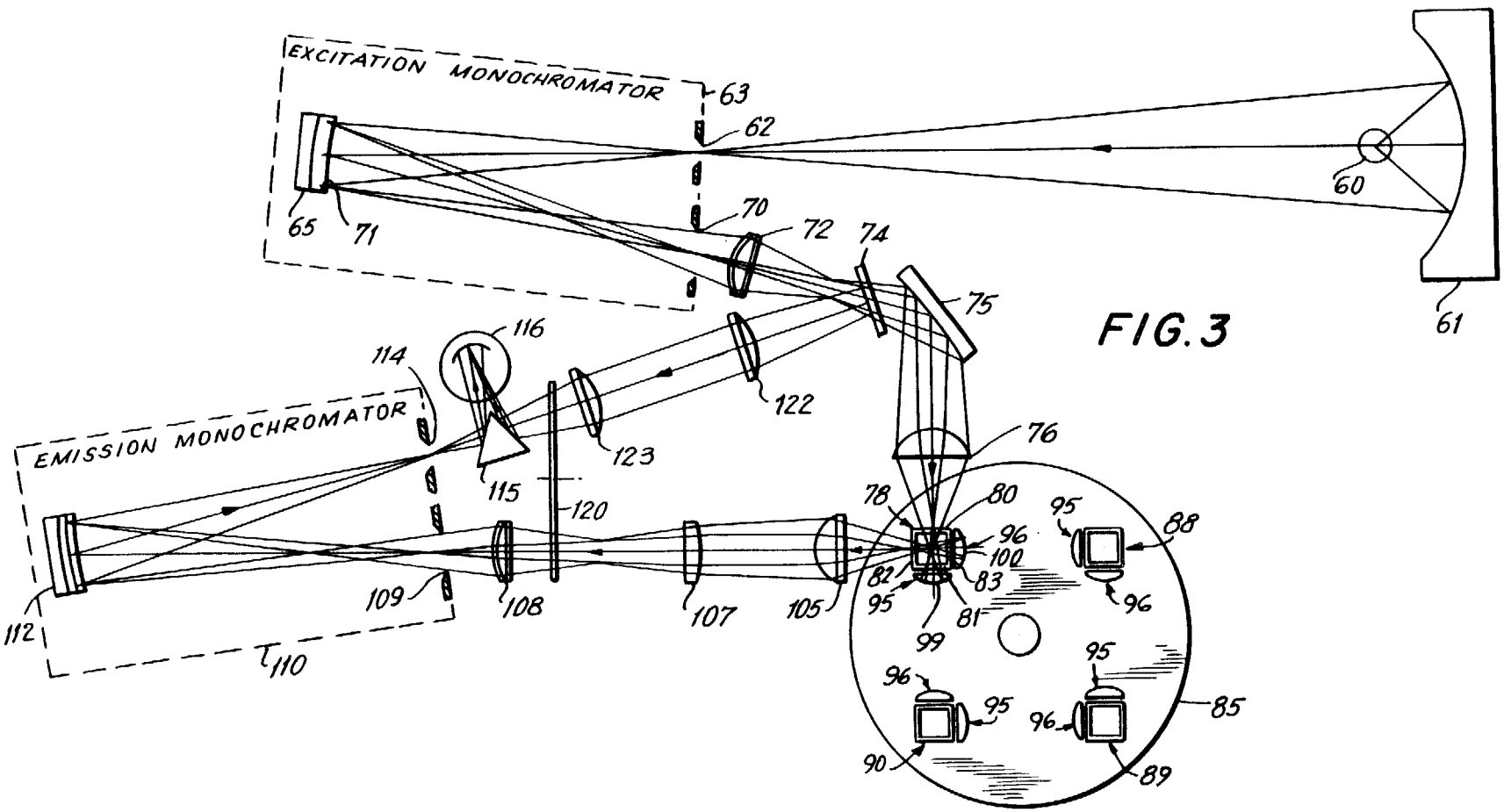
FIG. 3 is a simplified schematic plan view of a fluorescence spectrophotometer in accordance with another illustrative embodiment of the invention.
Figure 4:
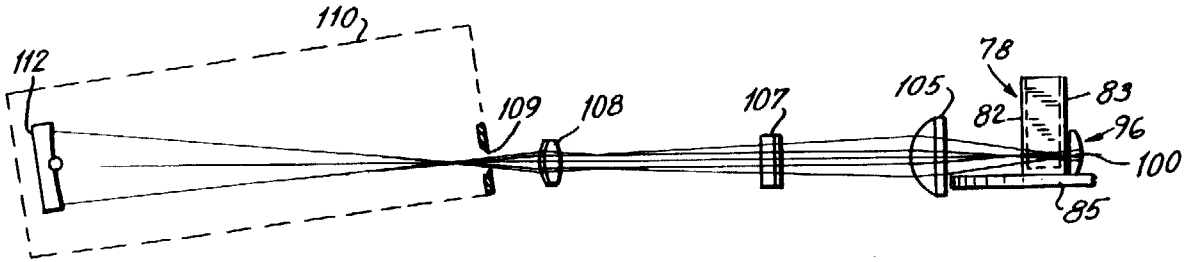
FIG. 4 is a simplified schematic elevational view of a portion of the spectrophotometer of FIG. 3, as seen from the line 4—4 in FIG. 3.

In each of the illustrated embodiments of the invention the excitation and emission beams are directed back for a second pass through the sample by the concave spherical mirrors 32 and 37 (FIG. 1) or by the concave spherical mirrors 95 and 96 (FIG. 3). One advantage of this arrangement over the conventional use of flat mirrors is that the radiation reflected by each mirror illuminates approximately the same volume of the sample as the radiation approaching the mirror. Extraneous signals due to scattering effects are thus maintained at a minimum, and substantially the full benefit of the mirrors is achieved in providing the desired increase in intensity.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

[1. Apparatus for measuring radiation from a sample, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit, and means for directing the excitation beam through said excitation exit slit;

means cooperating with the excitation monochromator means for directing the excitation beam to said sample and for forming an image of the excitation exit slit adjacent the sample;

emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

means cooperating with the emission monochromator means for directing the emission beam to the emission entrance slit and for forming an image of said emission entrance slit adjacent the sample;

said excitation beam and said emission beam having principal rays which intersect at said sample, and each of said images having a longitudinal axis which lies in the plane defined by said principal rays; and radiation detecting means for receiving the monochromatic radiation from the exit slit of the emission monochromator means.]

[2. Apparatus as defined in claim 1, in which the longitudinal axis of the excitation exit slit image extends in a direction parallel to the principal ray of the emission beam, and the longitudinal axis of the emission entrance slit image extends in a direction parallel to the principal ray of the excitation beam.]

3. Apparatus [as defined in claim 1, in which] each of said images [is anamorphic] *being anamorphically*

*distorted; for measuring fluorescent radiation from a sample, the apparatus comprising, in combination:*

*a source of radiation;*

*excitation monochromator means for isolating an excitation beam of monochromatic radiation from said source, the excitation monochromator means having an excitation entrance slit for receiving radiation from said source, an excitation exit slit, and means for directing the excitation beam through said excitation exit slit;*

*means cooperating with the excitation monochromator means for directing the excitation beam to said sample and for focusing an image of the excitation exit slit on the sample;*

*emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;*

*means cooperating with the emission monochromator means for directing the emission beam to the emission entrance slit and for focusing an image of said emission entrance slit on the sample;*

*means for introducing distortion in each of said images;*

*said excitation beam and said emission beam having principal rays which intersect at said sample, and each of said images having a longitudinal axis which lies in the plane defined by said principal rays, each point along said emission entrance slit being filled with radiation of equal intensity corresponding to irradiation of the sample with radiation from substantially the entire length of said excitation exit slit; and*

*radiation detecting means for receiving the monochromatic radiation from the exit slit of the emission monochromator means.*

[4. Apparatus for measuring radiation from a sample, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit, and means for directing the excitation beam through said excitation exit slit;

means cooperating with the excitation monochromator means for directing the excitation beam to said sample and for forming an image of the excitation exit slit adjacent the sample;

emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

means cooperating with the emission monochromator means for directing the emission beam to the emission entrance slit and for forming an image of said emission entrance slit adjacent the sample;

said excitation beam and said emission beam having principal rays which intersect at said sample, and each of said images having a longitudinal axis which lies in the plane defined by said principal rays, the excitation exit slit and the emission entrance slit having longitudinal axes which extend in directions perpendicular to said plane; and radiation detecting means for receiving the monochromatic radiation from the exit slit of the emission monochromator means.]

[5. Apparatus for measuring radiation from a sample, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit, and means for directing the excitation beam through said excitation exit slit;

means cooperating with the excitation monochromator means for forming an image of said excitation exit slit adjacent said sample;

emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

means cooperating with the emission monochromator means for forming an image of said emission entrance slit adjacent said sample;

said excitation beam and said sample beam having principal rays which intersect at said sample, and each of said images having a longitudinal axis which lies in the plane defined by said principal rays; and radiation detecting means for receiving the monochromatic radiation from the exit slit of the emission monochromator means.]

[6. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit, and means for directing the excitation beam through said excitation exit slit;

a first optical system cooperating with the excitation monochromator for forming a real image of said excitation exit slit in close juxtaposition with a first surface of said sample;

emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

a second optical system cooperating with the emission monochromator means for forming an image of said emission entrance slit in close juxtaposition with a second surface of said sample;

said excitation beam and said sample beam having principal rays which intersect at said sample, and each of said images having a longitudinal axis which lies in the plane defined by said principal rays; and radiation detecting means for receiving the monochromatic radiation from the exit slit of the emission monochromator means.]

[7. Apparatus as defined in claim 6, which further comprises, in combination:

reflective means in facing relationship with a third and a fourth surface of said sample in position to direct radiation from said excitation base and said sample back toward said sample.]

[8. Apparatus as defined in claim 6, in which each of said optical systems includes a pair of mirrors oriented at 45° angles with respect to the principal ray of the radiation incident thereto.]

[9. Apparatus as defined in claim 8, in which one of the mirrors in each said pair is spherically concave.]

[10. Apparatus for measuring radiation from a sample, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

means cooperating with the excitation monochromator means for directing the excitation beam to said sample and for forming first and second images adjacent the sample of the respective first and second limiting apertures;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means defining a fourth limiting aperture for the emission beam;

means cooperating with the emission monochromator means for directing the emission beam to the emission entrance slit and for forming third and fourth images adjacent the sample of the respective third and fourth limiting apertures;

said excitation beam and said emission beam having principal rays which intersect at said sample;

radiation detecting means for receiving the monochromatic radiation from the exit slit of the emission monochromator means.]

[11. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

means cooperating with the excitation monochromator means for forming a first image of said first limiting aperture adjacent a first surface of said sample and a second image of said second limiting aperture adjacent a second surface of said sample;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means defining a fourth limiting aperture for the emission beam;

means cooperating with the emission monochromator means for forming a third image of said third limiting aperture adjacent a third surface of said sample and a fourth image of said fourth limiting aperture adjacent a fourth surface of said sample;

said excitation beam and said emission beam having principal rays which intersect at said sample, and each of said images having a longitudinal axis which lies in the plane defined by said principal rays; and radiation detecting means for receiving the monochromatic radiation from the exit slit of the emission monochromator means.]

[12. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

a first optical system cooperating with the excitation monochromator means for forming a first image of said first limiting aperture adjacent a first surface of said sample and a second image of said second limiting aperture adjacent a second surface of said sample;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means defining a fourth limiting aperture for the emission beam;

a second optical system cooperating with the emission monochromator means for forming a third image of said third limiting aperture adjacent a third surface of said sample and a fourth image of said fourth limiting aperture adjacent a fourth surface of said sample;

said excitation beam and said emission beam having principal rays which intersect at said sample, and each of said images having a longitudinal axis which lies in the plane defined by said principal rays;

the longitudinal axis of said first image extending in a direction parallel to the principal ray of the emission beam, and the longitudinal axis of said third image extending in a direction parallel to the principal ray of the excitation beam; and radiation detecting means for receiving the monochromatic radiation from the exit slit of the emission monochromator means.]

[13. Apparatus as defined in claim 12, in which the longitudinal axis of said second image extends in a direction parallel to the principal ray of the emission beam, and the longitudinal axis of said fourth image extends in a direction parallel to the principal ray of the excitation beam.]

14. Apparatus for measuring *fluorescent* radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

a first optical system for directing the excitation beam toward said sample, the first optical system forming a first [anamorphic] *anamorphically distorted* image of said first limiting aperture adjacent a first surface of said sample and forming a second [anamorphic] *anamorphically distorted* image of said second limiting aperture adjacent a second surface of said sample, *said first and second sample surfaces being in spaced opposed relationship with each other;* emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means defining a fourth limiting aperture for the emission beam;

a second optical system for receiving the emission beam from said sample and directing the same to the entrance slit of the emission monochromator means, the second optical system forming a third [anamorphic] *anamorphically distorted* image of said third limiting aperture adjacent a third surface of said sample and forming a fourth [anamorphic] *anamorphically distorted* image of said fourth limiting aperture adjacent a fourth surface of said sample, *said third and fourth sample surfaces being in spaced opposed relationship with each other and being angularly disposed with respect to said first and second sample surface;* said excitation beam and said emission beam having principal rays which intersect at the sample, and each of said images having a longitudinal axis which lies in the plane defined by said principal rays; and radiation detecting means for receiving the monochromatic radiation from the exit slit of the emission monochromator means.

15. Apparatus as defined in claim 14, in which the excitation beam has extreme rays between said first and second images which illuminate a volume of said sample in the approximate shape of a right rectangular prism, and the emission beam has extreme rays between said third and fourth images which are illuminated by radiation from a volume of said sample in the approximate shape of a right rectangular prism.

[16. Apparatus for measuring radiation from a sample having pairs of opposed surfaces, the apparatus comprising, in combination:

a source of radiation;

excitation monochromator means for isolating a monochromatic beam of radiation from said source, the excitation monochromator means having an excitation entrance slit for receiving radiation from said source, an excitation exit slit defining a first limiting aperture, and means for directing the monochromatic beam through said excitation exit slit, the excitation monochromator means including means defining a second limiting aperture for the monochromatic beam;

means cooperating with the excitation monochromator means for dividing the monochromatic beam into an excitation beam and a reference beam;

a first optical system for directing the excitation beam toward said sample, the first optical system forming a first image of said first limiting aperture adjacent a first surface of said sample and forming a second image of said second limiting aperture adjacent a second surface of said sample;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means defining a fourth limiting aperture for the emission beam;

a second optical system for receiving the emission beam from said sample and directing the same to the entrance slit of the emission monochromator means, the second optical system forming a third image of said third limiting aperture adjacent a third surface of said sample and forming a fourth image of said fourth limiting aperture adjacent a fourth surface of said sample;

said excitation beam and said emission beam having principal rays which intersect at the sample, and each of said images having a longitudinal axis which lies in the plane defined by said principal rays;

radiation detecting means for receiving the monochromatic radiation from the exit slit of the emission monochromator means; and means for receiving said reference beam and for directing the same to said radiation detecting means.]

[17. Apparatus as defined in claim 16, in which the reference beam receiving means includes a rotary chopper in position to alternately interrupt said reference beam and said emission beam.]

[18. Apparatus as defined in claim 16, in which the longitudinal axis of said first and second images extend in directions parallel to the principal ray of the emission beam, and the longitudinal axes of said third and fourth images extend in directions parallel to the principal ray of the excitation beam.]

[19. Apparatus as defined in claim 16 which further comprises, in combination:

a rotary support member for pivoting said sample into a position in which said first sample surface is in facing relationship with the excitation beam and said third sample surface is in facing relationship with the emission beam.]

[20. Apparatus as defined in claim 16, in which the first optical system, the second optical system and the reference beam receiving means are optically equal to one another.]

[21. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit, and means for directing the excitation beam through said excitation exit slit;

means cooperating with the excitation monochromator for forming a first distorted image of said excitation exit slit adjacent said sample;

emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

means cooperating with the emission monochromator means for forming a second distorted image of said emission entrance slit adjacent said sample, said second distorted image having a length to width ratio equal to that of said first distorted image;

said excitation beam and said sample beam having principal rays which intersect at said sample;

reflective means including a pair of concave reflecting surfaces adjacent said sample in position to receive the respective excitation and emission beams from said sample and to direct the beams back through the sample for a second pass, each of said beams traversing approximately the same volume of the sample as the beam approaches and is reflected by the corresponding reflecting surface; and radiation detecting means for receiving the monochromatic radiation from the exit slit of the emission monochromator means.]

[22. Apparatus as defined in claim 21, in which each of said reflecting surfaces is spherically concave.]

[23. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

means cooperating with the excitation monochromator means for forming a first image of said first limiting aperture adjacent a first surface of said sample and a second image of said second limiting aperture adjacent a second surface of said sample;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means defining a fourth limiting aperture for the emission beam;

means cooperating with the emission monochromator means for forming a third image of said third limiting aperture adjacent a third surface of said sample and a fourth image of said fourth limiting aperture adjacent a fourth surface of said sample;

said excitation beam and said emission beam having principal rays which intersect at said sample;

reflective means including a pair of concave reflecting surfaces adjacent said sample in position to receive the respective excitation and emission beams from said sample and to direct the beams back through the sample for a second pass, each of said beams traversing approximately the same volume of the sample as the beam approaches and is reflected by the corresponding reflecting surface; and radiation detecting means for receiving the monochromatic radiation from the exit slit of the emission monochromator means.]

[24. Apparatus for measuring radiation from a sample, the apparatus comprising, in combination:

a source of radiation;

excitation monochromator means for isolating monochromatic radiation from said source, the excitation monochromator means receiving radiation from said source and having an excitation exit slit defining a first aperture and means including a second aperture for directing a part of the received radiation through said excitation exit slit in the form of a monochromatic excitation beam;

first means cooperating with the excitation monochromator means for directing the excitation beam to said sample and for forming an image of the excitation exit slit adjacent the sample;

emission monochromator means for isolating radiation from said sample, the emission monochromator means having an emission entrance slit for receiving an emission beam of radiation from said sample;

second means cooperating with the emission monochromator means for directing the emission beam to the emission entrance slit and for forming an image of said emission entrance slit adjacent the sample;

said excitation beam and said emission beam intersecting at said sample; and radiation detecting means for receiving monochromatic radiation from the emission monochromator means;

said first and second beam directing means including means for forming the respective slit images adjacent said sample with their longitudinal axes lying in the plane defined by said intersecting beams.]

[25. Apparatus for measuring radiation from a sample, the apparatus comprising, in combination:

a source of radiation;

excitation monochromator means for isolating an excitation beam of monochromatic radiation from said source, the excitation monochromator means receiving radiation from said source, the excitation monochromator means receiving radiation from said source and having an excitation exit slit defining a first aperture and means including a second aperture for directing a part of the received radiation through said excitation exit slit in the form of a monochromatic excitation beam;

first means cooperating with the excitation monochromator means for directing the excitation beam to said sample and for forming a distorted image of the excitation exit slit adjacent the sample;

emission monochromator means for isolating radiation from said sample, the emission monochromator means having an emission entrance slit for receiving an emission beam of radiation from said sample;

second means cooperating with the emission monochromator means for directing the emission beam to the emission entrance slit and for forming a distorted image of said emission entrance slit adjacent the sample;

said excitation beam and said emission beam having axial rays which intersect at said sample; and radiation detecting means for receiving the monochromatic radiation from the emission monochromator means;

said first and second beam directing means including means for forming said distorted slit images with their longitudinal axes lying in a plane defined by said intersecting beams.]

[26. Apparatus as defined in claim 25 wherein the exit slit of said excitation monochromator means and the entrance slit of said emission monochromator means are both horizontal.]

[27. Apparatus as defined in claim 25 wherein the exit slit of said excitation monochromator and the entrance slit of said emission monochromator are both vertical, said first and second beam directing means including means for rotating said images ninety degrees.]

28. Apparatus for measuring *fluorescent* radiation from a sample, the apparatus comprising, in combination:

a source of radiation;

excitation monochromator means for isolating an excitation beam of monochromatic radiation from said source, the excitation monochromator means including means defining first and second limiting apertures;

first means cooperating with the excitation monochromator means for directing the excitation beam to said sample and for [forming] *focusing* a first *anamorphically* distorted image [adjacent] *on* the sample of one of said first and second limiting apertures, said first *anamorphically* distorted image having a length to width ratio larger than the length to width ratio of the corresponding aperture;

emission monochromator means for isolating an emission beam of radiation from said sample, the emission monochromator means including means defining third and fourth limiting apertures;

second means cooperating with the emission monochromator means for directing the emission beam to the emission monochromator means and for [forming] *focusing* a second *anamorphically* distorted image [adjacent] *on* the sample of one of said third and fourth limiting apertures, said second *anamorphically* distorted image having a length to width ratio equal to that of said first distorted image and larger than the length to width ratio of the corresponding aperture;

said excitation beam and said emission beam having axial rays which intersect at said sample, and each of said images having a longitudinal axis which lies in the plane defined by said intersecting [beams] *rays*; and radiation detecting means for receiving monochromatic radiation from the emission monochromator means.

29. Apparatus as defined in claim 28 wherein said first and second beam directing means respectively [form] *focus* third and fourth distorted images [adjacent] *on* the sample of the other limiting apertures.

30. Apparatus as defined in claim 29 wherein the *sample has pairs of opposed sides, and wherein the* distorted images of the apertures of the excitation monochromator means are respectively adjacent two opposite sides of said sample and the distorted images of the apertures of the emission monochromator means are respectively adjacent two other opposite sides of said sample.

31. Apparatus as defined in claim 30 wherein the distorted images of said apertures adjacent said sample all have approximately the same length.

* * * * *